(12) United States Patent
Akkus et al.

(10) Patent No.: US 10,017,868 B2
(45) Date of Patent: Jul. 10, 2018

(54) ELECTROCHEMICAL PROCESSING OF MATERIALS, METHODS AND PRODUCTION

(71) Applicant: CASE WESTERN RESERVE UNIVERSITY, Cleveland, OH (US)

(72) Inventors: Ozan Akkus, Brooklyn, OH (US); Vipuil Kishore, Shaker Heights, OH (US); Mousa Younesi, Shaker Heights, OH (US); Anowarul Islam, Shaker Heights, OH (US)

(73) Assignee: CASE WESTERN RESERVE UNIVERSITY, Cleveland, OH (US)

( * ) Notice: Subject to any disclaimer, the term of this patent is extended or adjusted under 35 U.S.C. 154(b) by 240 days.

(21) Appl. No.: 14/766,656

(22) PCT Filed: Feb. 11, 2014

(86) PCT No.: PCT/US2014/015683
§ 371 (c)(1),
(2) Date: Aug. 7, 2015

(87) PCT Pub. No.: WO2014/126876
PCT Pub. Date: Aug. 21, 2014

(65) Prior Publication Data
US 2015/0376806 A1    Dec. 31, 2015

Related U.S. Application Data

(60) Provisional application No. 61/763,732, filed on Feb. 12, 2013.

(51) Int. Cl.
*C25D 1/18* (2006.01)
*A61L 27/24* (2006.01)
(Continued)

(52) U.S. Cl.
CPC ............ *C25D 1/18* (2013.01); *A61L 26/0033* (2013.01); *A61L 27/24* (2013.01); *A61L 27/26* (2013.01);
(Continued)

(58) Field of Classification Search
CPC ...... A61L 27/24; A61L 26/0033; A61L 27/26; C07K 14/78; B05D 1/18; C25D 1/18; D01D 5/0076; D01F 4/00
See application file for complete search history.

(56) References Cited

U.S. PATENT DOCUMENTS

| | | | |
|---|---|---|---|
| 1,975,504 A | 10/1934 | Formhals | |
| 4,470,498 A * | 9/1984 | Lund | B27N 3/26 198/382 |

(Continued)

*Primary Examiner* — Shogo Sasaki
(74) *Attorney, Agent, or Firm* — Hudak, Shunk & Farine Co. LPA

(57) ABSTRACT

Electrochemically aligned and compacted molecules, nanoparticles and microparticles with ampholytic nature, such as collagen, elastin, keratin and charged nanoparticle materials, methods of making and using the materials and associated production-related devices. In one embodiment, a device for producing continuous electrochemically aligned strands, threads or fibers is disclosed. In a further embodiment, fabrication of compositionally and geometrically complex anatomical forms by 3D-electrochemical compaction of biomolecules is disclosed. In yet another embodiment, methods for fabricating patterned lattice structures, in particular having controlled pore size and morphology, and the lattice structures themselves are also disclosed.

13 Claims, 11 Drawing Sheets

(51) Int. Cl.
*A61L 26/00* (2006.01)
*A61L 27/26* (2006.01)
*B05D 1/18* (2006.01)
*D01D 5/00* (2006.01)
*D01F 4/00* (2006.01)
*C07K 14/78* (2006.01)

(52) U.S. Cl.
CPC ............ *B05D 1/18* (2013.01); *D01D 5/0076* (2013.01); *D01F 4/00* (2013.01); *C07K 14/78* (2013.01)

(56) References Cited

U.S. PATENT DOCUMENTS

| | | | |
|---|---|---|---|
| 6,330,946 B1 * | 12/2001 | Allen | B03C 1/12 |
| | | | 209/219 |
| 7,375,404 B2 | 5/2008 | Park et al. | |
| 7,981,353 B2 | 7/2011 | Mitchell | |
| 9,666,852 B2 * | 5/2017 | Anandan | H01M 2/18 |
| 2002/0090725 A1 | 7/2002 | Simpson et al. | |
| 2010/0311949 A1 | 12/2010 | Akkus et al. | |
| 2011/0306754 A1 | 12/2011 | Cheng et al. | |
| 2012/0003893 A1 | 1/2012 | Branham | |
| 2016/0099453 A1 * | 4/2016 | Anandan | H01M 2/18 |
| | | | 429/142 |
| 2017/0029339 A1 * | 2/2017 | Weaver | B05D 7/24 |
| 2017/0029340 A1 * | 2/2017 | Weaver | C04B 35/80 |
| 2017/0126087 A1 * | 5/2017 | Soderberg | H02K 21/042 |
| 2017/0263904 A1 * | 9/2017 | Anandan | H01M 2/18 |

\* cited by examiner

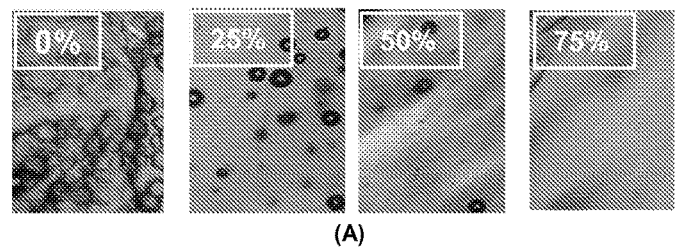
(A)
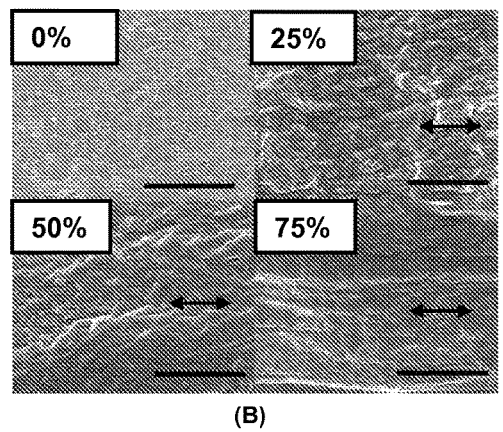
(B)
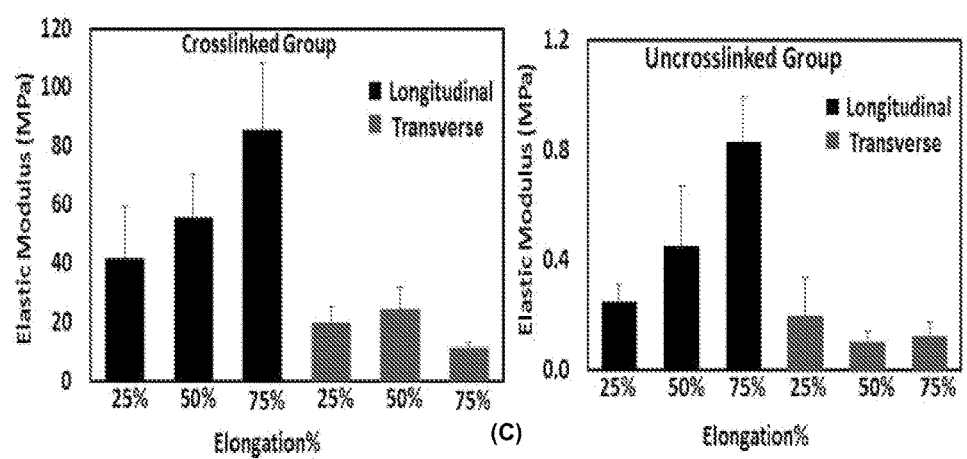
(C)
FIG. 12A-C

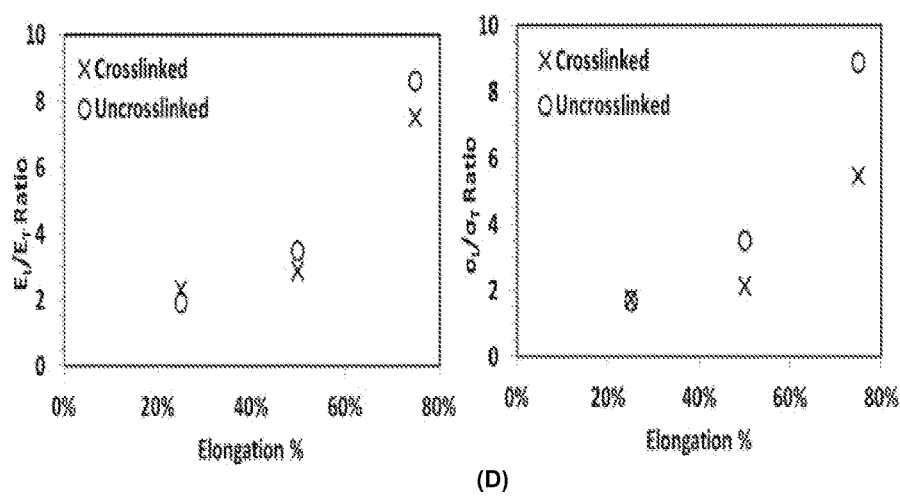
(D)
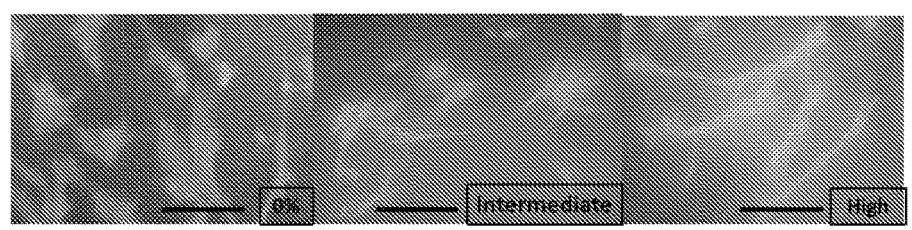
(E)
FIG. 12D-E

ELECTROCHEMICAL PROCESSING OF MATERIALS, METHODS AND PRODUCTION

FIELD OF THE INVENTION

The present invention relates to electrochemically aligned and compacted molecules, nanoparticles and microparticles with ampholytic nature, such as collagen, elastin, keratin and charged nanoparticle materials, methods of making and using the materials and associated production-related devices. In one embodiment, a device for producing continuous electrochemically aligned strands, threads or fibers is disclosed. In a further embodiment, fabrication of compositionally and geometrically complex anatomical forms by 3D-electrochemical compaction of biomolecules is disclosed. In yet another embodiment, methods for fabricating patterned lattice structures, in particular having controlled pore size and morphology, and the lattice structures themselves are also disclosed.

BACKGROUND OF THE INVENTION

Collagen nano-rod is the ubiquitous brick that endows many tissues with form and structural soundness. Furthermore, collagen molecules constitute a niche that is conducive to cell adhesion, motility, proliferation and biodegradation. That is why, collagen is situated at the center of biomaterial and tissue engineering applications. While the natural collagen-rich tissues have impressive capacity to bear mechanical loads, the mechanical properties of reconstituted collagen has the consistency of a gel; thus, its applications are generally non-load bearing. The major discord between collagen in a native tissue matrix and reconstituted collagen gels is the degree of compaction of the collagen molecules. Fabrication collagen in mechanically robust forms would enable the repair mechanically demanding tissues such as tendons, ligaments, blood vessels, heart valves, trachea, craniofacial and dental tissues.

Tendon-repair procedures occur in excess of 100,000 annually in the U.S. alone costing approximately $30 billion dollars. Such injuries arise from trauma and various degenerative conditions in anatomical locations including the rotator cuff, Achilles tendon and patellar tendon. The incidence is expected to increase with the aging of the population. Often, the injury extends to the bulk of the tendon and is irreparable by suturing.

Tendon injuries may impose grave consequences to the quality of life of an individual. Being the critical unit responsible for transmitting the force generated by the muscles to the bones, an injured tendon results in partial or complete loss in the range of motion of the involved joint. Therefore, repairing gaps to restore the length of the tendon is critical to the success of the surgical repair. Unfortunately, tendons are relatively poorly vascularized limiting their regenerative capacity. Also, tendon regenerates only partially and slowly; animal models of tendon repair where healing is left to occur naturally indicate that the tendon gains 10% of its original strength by 3 months and 50% by 1.5 years. Another issue, particularly with the repair of chronic tendionopathies, is the failure of repair (as high as 20%-95% for the rotator cuff). Cost and suffering associated with repetitive surgeries is a major drawback. Therefore, regenerative solutions which would expedite tendon repair, enable earlier mobilization and reduce failure rates would be highly significant by reducing costs and by improving the range of motion of involved joints.

Suture-based repair is insufficient when a substantial volume of the tendon needs repair, calling for bulk materials for reconstructing the defect. Autografts are the primary choice of surgeons for bulk tendon repair, except that compromising an otherwise healthy tendon for autograft harvest is a major drawback. Morbidity can be associated with donor site. Also, autografts have limited availability. Allografts or xenografts (e.g. porcine skin or subintestinal mucosa) derivatives are other venues for tendon repair. Immune response due to non-collagenous or cellular content, and disease transmission are major concerns for allografts and xenografts. Also, allograft/xenograft performance may be unpredictable because product quality is a function of the donor. Non-degradable synthetic polymers have been used in tendon repair; however, foreign body reaction to these polymers is a significant drawback. It is possible that the optimal solution for tendon repair involves a strategy that will synergize a bioactive scaffold and cells.

Realization of the regeneration of the bulk tendon faces multiple challenges due to the absence of a bioscaffold platform which unifies the following characteristics: a) mechanical competence, b) ability to be populated by cells, c) ability to induce tenogenic differentiation of mesenchymal stem cells (MSCS), AND, d) form and size that can be integrated to the repair site surgically.

Collagen biomolecule is a nanorod which is essentially the basic building block of all load bearing tissues in the body. When collagen monomers are reconstituted, they attain a mechanically inferior gel consistency. Fabrication methods which would process collagen material to mechanically competent and anatomically complex shapes would improve the reconstruction of tendons, bones, joint surfaces, cranial defects, ears, nose and other tissues.

Methods for electrochemical processing of collagen-rich solutions which generate density backed and mechanically robust sheet layers are known.

Recent efforts in the field of tissue engineering to develop scaffolds for cartilage regeneration have shown promise; however, clinical translation of existing scaffolds is limited due to shortcomings in generating cartilaginous tissue that is matching the mechanical properties and the hierarchical structure of native cartilage. Another significant challenge is making these constructs in a fashion to conform to the complex geometry of human joints. An anatomically conforming construct that mimics the composition and mechanical properties of native cartilage would be significant by providing compositional and topographical cues to stimulate chondrogenesis and to promote the formation of neo-cartilage. Cartilage tissue engineering integrates cell-biomaterial complexes to defect site (injectable, solid form scaffolds, scaffold-free strategies etc.). Despite intense studies on tissue engineering of cartilage, there are significant roadblocks.

One challenge is inferior mechanical properties of constructs. Cartilage is a load-bearing tissue and the demand on the mechanical end is significant. Existing scaffolds (such as agarose, synthetic biopolymers etc.) lack mechanical robustness and most studies strategize to attain mechanical rigidity by the synthetic action of the seeded cells during culture period, less so by the scaffolds.

Another challenge is associated with the size of the defect that can be repaired. In general, the majority of existing modalities are limited to repair of early-stage focal defects using flat disc-shaped scaffolds. There are not many technologies which would allow repairing large defects (partial or full joint) expanding over curved planes. To date, other than woven PLA sheets, attempts on large non-conforming defect repair have been limited.

A further challenge is the multiphasic integration where the scaffold needs to conjoin with host cartilage in the periphery and bone at its base. Focal repair scaffolds have not been highly successful in lateral integration with the host cartilage. Partial or total surface replacement may circumvent this issue by limiting the integration problem to the bone at the base of the scaffold.

Scaffolds used in tissue engineering of cartilage are synthetic biopolymers, natural ECM molecules and scaffold-free frameworks formed by cultured cells. Construction of synthetic biopolymers which provide groups conducive to cell adhesion and degradation involves chemical conjugation with associated time and material cost. Scaffold-free strategies have met with some success, but the current challenges involve limited mechanical properties and complex bioreactor conditions to manage the differentiation closely. From a practical point of view, using scaffolds which comprise native cartilage ECM molecules (i.e. type II collagen, glycosaminoglycans, proteoglycans) may be advantageous because these biomolecules present amino acid sequences recognizable by resident cells as well as they can be degraded and remodeled by cells. However, fabricating native molecules in a form and shape that matches the compositional gradient and mechanical robustness of cartilage is a significant challenge.

Transformations of monomeric collagen solutions to solid phase by electrochemical gradients induced by electrodes have been demonstrated.

SUMMARY OF THE INVENTION

In view of the above, a problem of the invention was solved by providing devices and methods for producing electrochemically aligned and compacted engineered materials, such as but not limited to, strands, threads, fibers, patterned structures and three dimensional structures from molecules, nanoparticles and microparticles with ampholytic nature, such as collagen, elastin, keratin and charged nanoparticle materials. As used herein, the term ampholytic nature is defined as a substance that has different charges at different pH values.

Another challenge of the present invention was to provide electrochemically aligned threads or fibers of a continuous or relatively long length, as well as a device that can be utilized to produce continuous length or elongated electrochemically aligned threads or fibers from the materials of interest. Obtainment of threads in continuous length is imperative to braiding or weaving the threads as biotextiles.

Yet another problem solved by the invention was to develop two-dimensional patterned lattice structures which have a controlled pore size and morphology.

Still another problem solved by the present invention was to provide three-dimensional structures and methods for forming the structures that can be created as geometrically complex and/or anatomical forms.

A further problem of the present invention was to provide structures, for example electrochemically aligned collagen (ELAC) structures, in the form of a tube that is useful in various embodiments as a conduit, for example a vein, artery, or the like.

An additional problem to be solved the by present invention was to provide naturally crosslinked structures, such as ELAC structures, which avoid the use of chemicals in order to allow use within a human or other living creature.

It is an object of the present invention to automate and scale up the fabrication of electrochemically aligned collagen (ELAC). With ELAC, uniform fabric orientation and close packing density result in mechanical properties which match those of the native tendon.

It is an additional object to optimize the morphology of woven ELAC scaffolds and to provide bio-active ELAC scaffolds that can be utilized to repair critical sized tendon defects.

Yet another object of the invention is to provide a rotating electrochemical aligning device which is able to provide ELAC threads in continuous strands of a desired length.

Still another object of the present invention is to provide improved mechanics and fabrication rate of electrocompacted layers.

Another object of the present invention is to provide multi-layered cellularized scaffolds.

A further object of the present invention is to provide an anatomically correct joint surface replacement scaffold.

A further object of the present invention is to provide a method to fabricate patterned lattice structures with controlled pore size and morphology, creating the potential of reconciling porosity and strength, one of the major roadblocks in engineering of load bearing tissues.

Still another object is to provide fabrication of scaffolds with controlled interconnected porosity, an essential feature for population of scaffold by cells and vasculature.

Yet another object of the present invention discloses patterned electrochemical deposition methods.

An additional object of the present invention is to provide three-dimensional complex porous or solid forms, wherein the forms are produced by electrochemical compaction of solutions comprising one of more of molecules, nanoparticles and microparticles with ampholytic nature, such as collagen, elastin, keratin and charged nanoparticle materials.

Accordingly, in one aspect of the invention a device for producing an electrochemically aligned strand is disclosed, comprising a solution reservoir for a solution comprising one of more of electrochemically alignable molecules, nanoparticles and microparticles with ampholytic nature (referred to as 'the solution' hereafter); a rotatable drum having a circumferential groove adapted to receive a portion of the solution from an outlet the solution reservoir, wherein at least two electrodes are present in the groove; and a collection device located downstream in a process line from the drum for receiving electrochemically aligned strands formed on the drum.

In a further aspect of the invention, a method for producing an electrochemically aligned strand is disclosed, comprising the steps of obtaining a device comprising a solution reservoir; a rotatable drum having a circumferential groove adapted to receive a portion of the solution from an outlet the solution reservoir, wherein at least two electrodes are present in the groove; and a collection reservoir located downstream in a process line from the drum for receiving electrochemically aligned strands formed on the drum; filling the collagen solution reservoir with a quantity of solution comprising one or more of electrochemically alignable molecules, nanoparticles and microparticles with ampholytic nature; applying the solution to a portion of the drum; applying an electric current to the solution during rotation of the drum; and transferring an electrochemically aligned strand formed on the drum from the solution to the collection reservoir.

Still another aspect of the invention is a device for producing sheets with geometrically complex forms by 2D compaction of biomolecules, comprising a first electrode disposed a distance from a second electrode, and a patterned form positioned between the electrodes, wherein the patterned form is unaltered by a current applied to the electrodes.

A further aspect of the invention is a method for producing sheets with geometrically complex patterns by 2D compaction of biomolecules, comprising the steps of: placing a patterned template between a first electrode and a second electrode disposed a distance from each other; supplying a solution comprising one or more of electrochemically compactable molecules, nanoparticles and microparticles with ampholytic nature to a portion of the patterned template; performing an electrochemical compaction process utilizing the device and creating a patterned structure from the solution; and separating the patterned structure from the patterned template.

In still another aspect of the invention a device for producing geometrically complex curviplanar forms by 3D compaction of biomolecules is disclosed, comprising a first electrode with 3D topography, a second electrode with a 3D topography positioned a distance from the first electrode and a solution comprising one of more of electrochemically compactable molecules, nanoparticles and microparticles with ampholytic nature is located between the first electrode and second electrode.

Another aspect of the invention is a method for producing geometrically complex forms by 3D compaction of biomolecules, comprising the steps of obtaining a device comprising a first electrode with a 3D topography, a second electrode with a 3D topography positioned a distance from the first electrode; placing a solution comprising one of more of electrochemically compactable molecules, nanoparticles and microparticles with ampholytic nature between the first electrode and second electrode; and performing an electrochemical compaction process on the solution utilizing the first electrode and second electrode and forming a 3D, compacted form.

BRIEF DESCRIPTION OF THE DRAWINGS

The invention will be better understood and other features and advantages will become apparent by reading the detailed description of the invention, taken together with the drawings, wherein:

FIGS. 12A-E illustrate tunable stiffness anisotropy can be achieved in electrocompacted forms, in particular sheets, wherein the variant images show A) 0% stretch shows no alignment (magenta) where as 75% extrusion gives the maximum alignment (blue). 25% and 50% stretch provide intermediate levels of alignment. B) SEM image shows that topography becomes aligned in stretching direction (stretching direction shown by the arrows; scale bar 2 µm). C) Transverse and longitudinal stiffness of crosslinked (left) and uncrosslinked (right) collagen sheets at different stretch levels. D) Stiffness (left) and failure stress (right) anisotropy in collagen sheets increased with stretch. E) Cytoskeletal morphology of MSCs at 0%, intermediate and high stretch levels (Scale bar 100 µm). The efficiency of the stretching process is improved after treating the collagen sheet in ethanol:water mixtures ranging from 10:90 by volume to 90:10 by volume.

DETAILED DESCRIPTION OF THE INVENTION

As indicated herein, the invention relates to devices and methods for producing electrochemically aligned and/or compacted engineered materials, such as but not limited to, strands, threads, fibers, patterned structures and three dimensional structures from one of more of molecules, nanoparticles and microparticles with ampholytic nature, such as collagen, elastin, keratin and charged nanoparticle materials, and the resulting engineered materials.

Fabrication of Electrochemically Aligned Threads and Bioscaffolds

Figure 1:
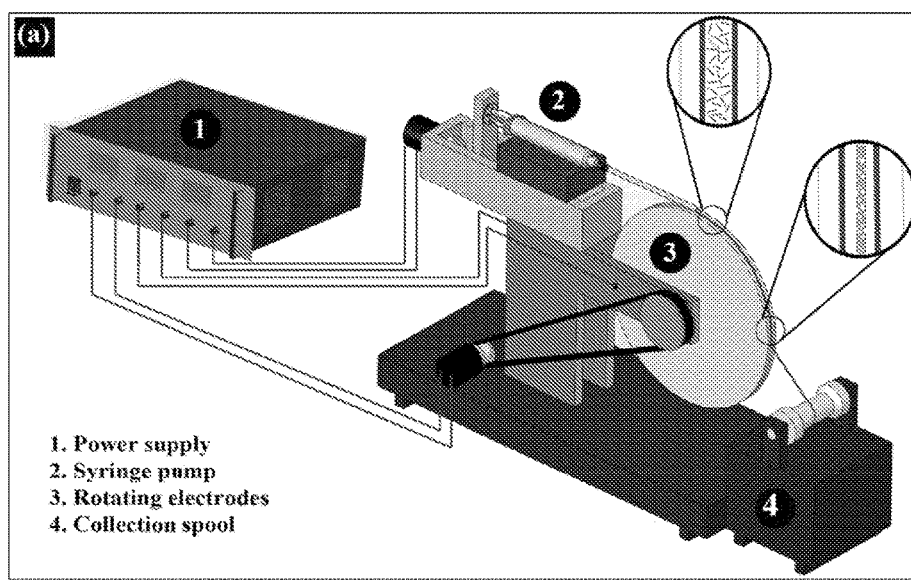
FIG. 1 illustrates one embodiment of a device that can be utilized to produce electrochemically aligned strands or threads.

One embodiment of an electrochemically aligned strand or thread production device, namely a robust rotating electrode electrochemical alignment device (REEAD) is shown in FIG. 1.

The basic components of REEAD include a syringe pump, a rotating electrode drum including at least two electrodes, a PBS sample incubation bath and a rotating collection spool positioned in the bath, see FIG. 1. The rotating electrode drum has a circumferential groove that is 2 mm in depth and 1.2 mm in width, in one embodiment. The depth and width of the groove can each be changed in various embodiments. Within the groove are two parallel electrode wires (for example stainless steel or platinum) that are 1 mm apart in one embodiment. This configuration provides an 'infinite' length electrode due to the constant rotation. As shown in FIG. 1, the syringe pump, i.e. electrochemically alignable solution source or reservoir applies a solution comprising one or more of electrochemically alignable molecules, nanoparticles and microparticles with ampholytic nature, such as a monomeric collagen solution in one embodiment, at the top of the drum via an outlet, the solution gets trapped in the groove and rotates with the drum. In one embodiment drum rotation speeds cover a range of about 0.1 to about 10 rpm. In one embodiment the solution is applied to the drum at a position that ranges from vertical to an angle of about 60° from vertical, and preferably from about vertical to about 45° from vertical, measured from a line extending from the center of the drum to the vertical top of the drum, in order to produce a desirable strand or thread prior to being removed from the drum. During rotation, the solution on the drum is subjected to the electric current, that ranges in one embodiment from about 0.1 to about 10 A and generally depends on the rotational speed of drum, and undergoes the packing and alignment which results in the electrochemically aligned thread by the time the drum completes a quarter turn (~15 sec). The thread is then released from the drum to a collection reservoir or bath of phosphate buffered saline kept at 37° C. to induce d-banding and spun onto a collection device, such as a spool situated in the bath. In some embodiments, a plurality of baths are provided between the electrode drum and the collection spool. The treatment solutions may include phosphate buffered saline or other ionic solutions, polymeric melts such as polylactic acid to coat threads, chemical crosslinking solutions such as genipin or glutaraldehyde, or biological molecules. Alternatively or in addition to the collection reservoir, the electrochemically aligned strand or thread can be wound directly onto a collection device and optionally a treatment solution can be applied therebetween, such as by, but not limited to, dropwise, spraying, coating, and brushing.

Figure 2A:
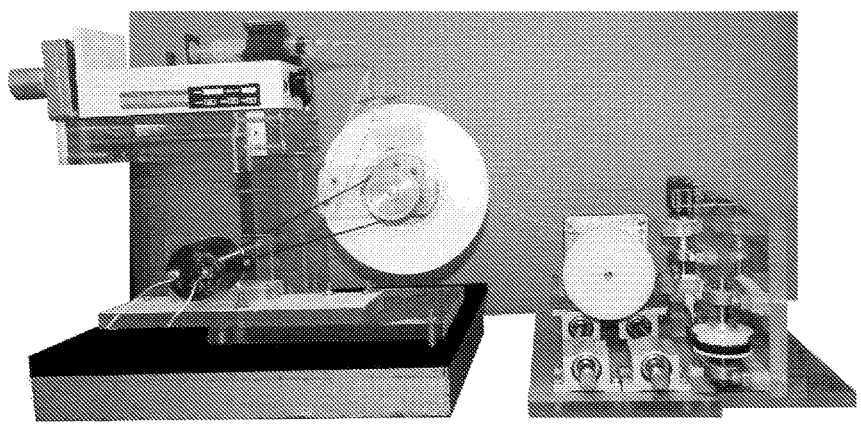
FIGS. 2A and 2B illustrate a further embodiment of an electrochemically aligned thread producing device in an upper perspective view and a partial view illustrating electrochemically aligned threads being produced, in particular ELAC threads, respectively.
Figure 2B:
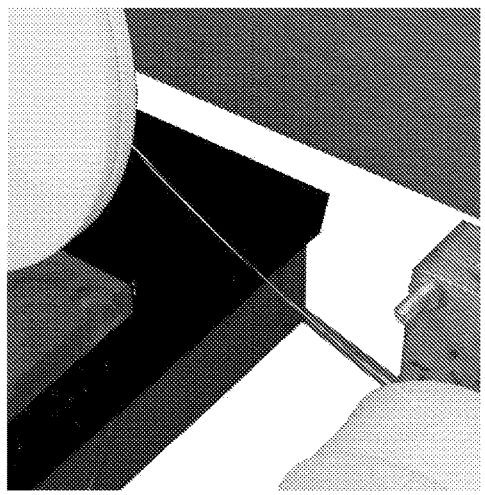

Electrochemically aligned threads have been successfully made using a working device, as shown in FIGS. 2A and 2B. The transmission of electric current to the electrodes in the rotating drum is achieved in a wire-free fashion, facilitated by sliding metal contacts. Other embodiments involve integrating DC motors, fine pitch backlash-free roller screws, bearings, gears and other mechanical components in a mechanical housing, see FIG. 1. One or more of the flow rate from the syringe, the rotational speed of the collection spool and the rotational speed of the mobile electrodes can be differentially controlled by a PC, using a built-in multichannel analog output card (National instruments) in one embodiment.

The embodiment illustrated in FIG. 1 includes motors connected to a power supply 1 which drive the syringe pump 2, the electrode drum 3 and the collection device, in particular a spool 4, respectively. The syringe is pushed via a threaded shaft. ELAC thread is shown wound on the spool. In one embodiment the motors are differentially controlled by an analog output card of a microprocessor in order to automate the process.

The ELAC threads can be synthesized in one embodiment as follows. An acid soluble monomeric collagen solution (Nutragen) can be diluted two-fold with ultrapure water to 3.0 mg/mL, dialyzed against ultrapure water for 18 hours, loaded between electrodes and electric current can be applied, for example at 30 Volts, 0.1 mA. Aligned collagen will can be incubated in a 1×PBS for 6 hours to promote fibril formation and crosslinked in 0.625% genipin in 90% ethanol for 3 days. The diameter of ELAC threads can be controlled between about 50 µm and about 400 µm by diluting the collagen solution and adjusting the electrode spacing for example between about 0.1 to about 10 mm in a preferred embodiment.

Figure 9A:
FIGS. 9A and 9B illustrate a further embodiment of an electrochemically aligned thread, in particular aligned cellulose nanoparticles or fibers, wherein A) is an image of aligned cellulose nanoparticles under polarized light and B) is an SEM image of a thread or strand made from cellulose nanofibers.
Figure 9B:
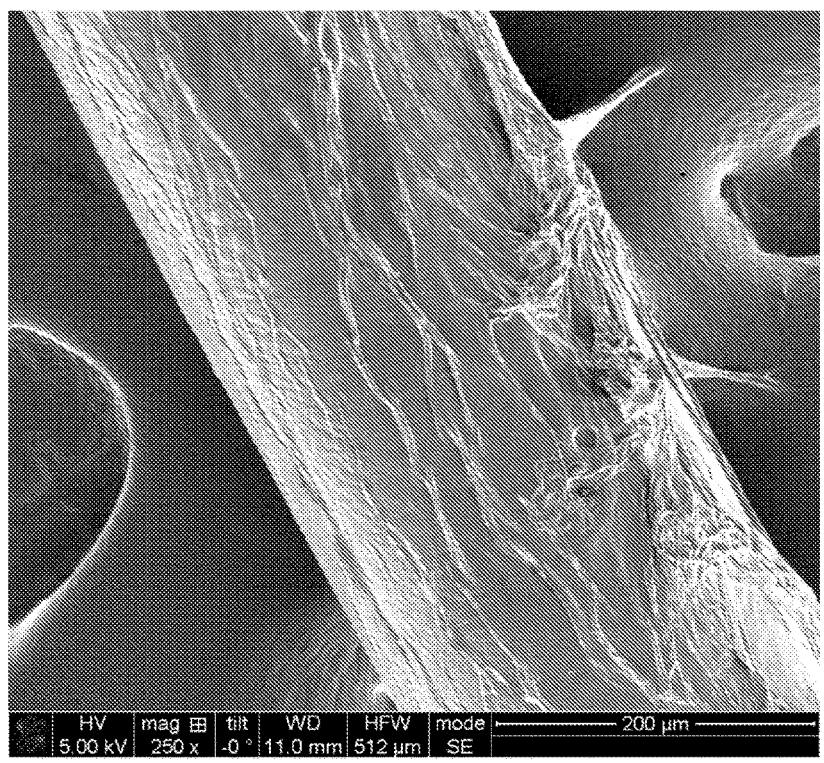
Figure 10:
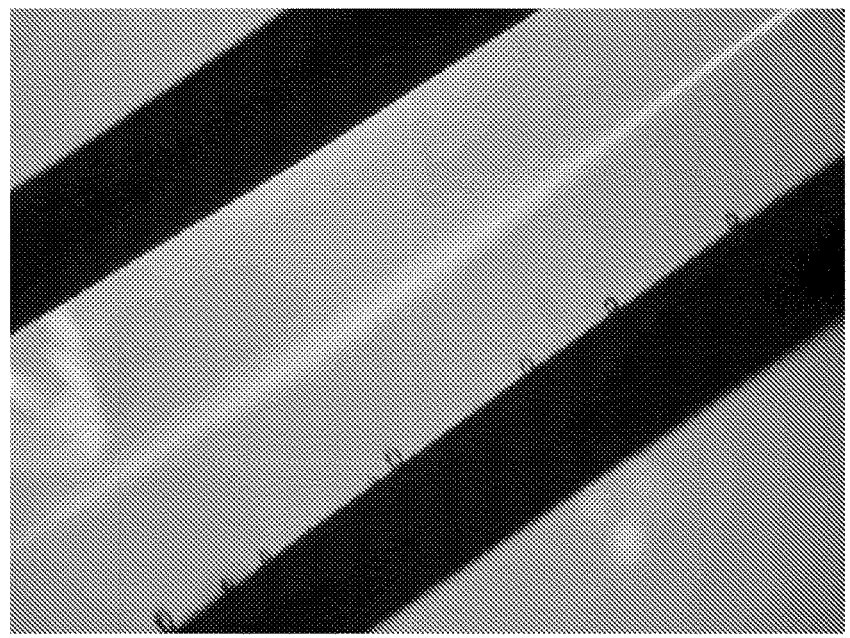
FIG. 10 illustrates a further embodiment of an electrochemically aligned strand or thread produced from elastin molecules wherein the image is taken under polarized light.
Figure 11:
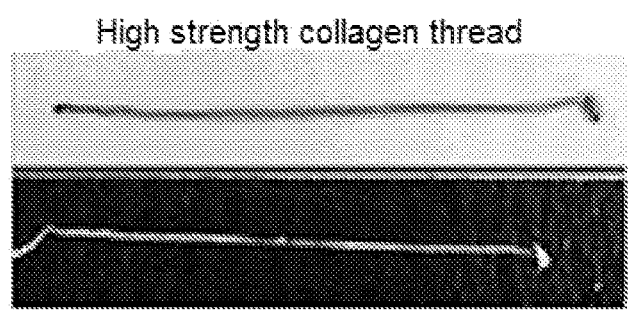
FIG. 11 illustrates an ELAC/hydroxyapatite composite aligned thread as compared to a collagen thread.

As indicated hereinabove, strands and thread can be formed from other proteins, for example elastin and keratin. FIG. 10 presents an image of elastin aligned fiber under polarized light. FIG. 11 illustrates composite electrochemically aligned strands or threads and particularly illustrates an ELAC/hydroxyapatite composite aligned thread. Electrochemically aligned and compacted materials, preferably strands or threads in one embodiment, can also be formed utilizing nanoparticles, for example cellulose nanoparticles. FIGS. 9A and B illustrate strands or threads of aligned cellulose nanoparticles.

Electrochemically aligned threads can be produced at different rates. Reduction speed can be varied by increasing or decreasing currents on the wires and by increasing or decreasing the rotation speed of the electrode drum. After the electrochemically aligned thread, such as ELAC thread, is collected on the collection device or spool, it can be incubated in a PBS solution and genipin crosslinking solution sequentially as described earlier. In an alternative embodiment, the electrochemically aligned strands, threads or the like are crosslinked using UV light after removal from the drum and prior to collection on the collection device.

In another embodiment the REEAD device includes a plurality of electrode sets in each drum, whereby multiple threads can fabricated simultaneously.

Figure 3:
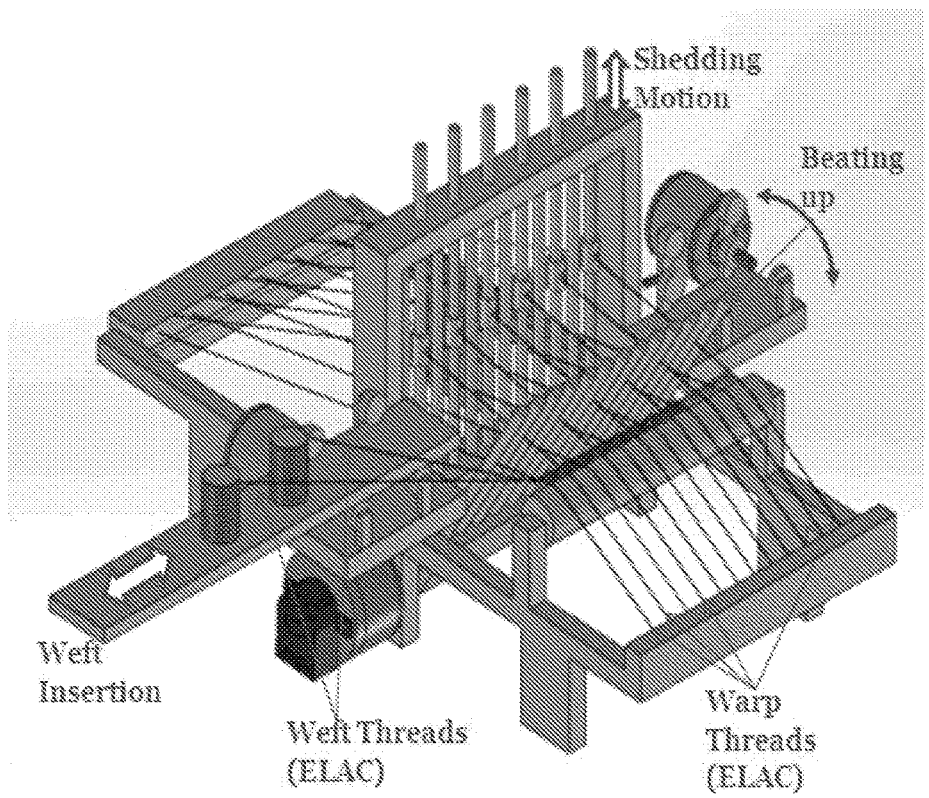
FIG. 3 illustrates one embodiment of an automated weaving loom, wherein in one embodiment the three weaving axes motions are driven by motors which are synchronized and controlled by a microprocessor.

As the size of tendons is at a relatively small scale, in the range of centimeters, a weaving loom such as illustrated in FIG. 3 is disclosed. The embodiment illustrates ELAC threads being woven. The electrochemically aligned thread weaving loom has the following components: 1) vertical motion frame that reciprocates the fixed length warp yarns (a.k.a. shedding), 2) a horizontal motion frame with a thread spool that performs the weft insertion between warps, and 3) a rotary reed that pushes the weft to from the woven cloth (a.k.a. beating up). Motors, gears, motion sensors and other mechanical components can be integrated as indicated in the design and computer control.

In various embodiments, the scaffold dimensions can vary. As continuous length electrochemically aligned threads can be fabricated, generally any construction that can be fabricated with a regular thread by weaving and/or braiding can be produced with electrochemically aligned threads. For example sheets can be prepared as large as a torso, or a rope can be fabricated of any length. Both ends of the scaffold are impregnated with a strip of polylactic acid in some embodiments. The impregnation serves the purpose of reinforcing the suture locations. Impregnation can be achieved by dipping the end region of the scaffold in PLA dissolved in chloroform, which is benign to collagen and used routinely for sterilizing collagen.

Fabrication of compositionally and geometrically complex anatomical forms by 2D and 3D electrochemical compaction of biomolecules.

Figure 4:
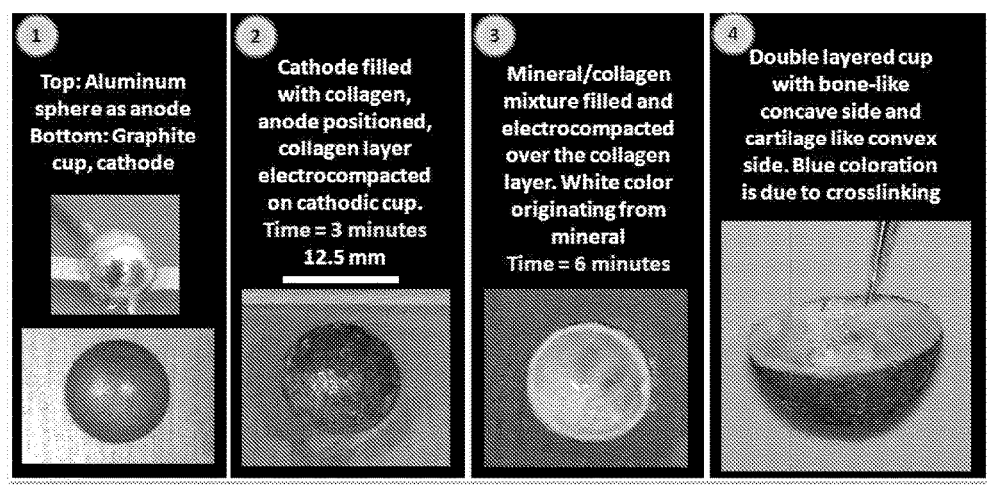
FIG. 4 illustrates one embodiment of a fabrication sequence used to obtain electrocompacted, multilayered curved surfaces.

By using electrodes with curved topographies, the electrochemical-compaction process (3d-ECOM) deposits 3D-freeform layers derived from compositions or solutions comprising the above-noted molecules, nanoparticles and microparticles with ampholytic nature, for example collagen layers, simultaneously and rapidly over the full field, see FIG. 4. Resulting layers can be seeded with cells and stacked sequentially to obtain cellularized complex tissue/organ forms. 3d-ECOM also emulates the compositional complexity of tissues by allowing the inclusion of additives such as mineral particles, other biomolecules and bioinductive growth factors.

Key process variables, for example compactant solution concentration, the electric current density and the electrode separation distance are varied systematically to increase the degree of compaction as well as to reduce the time frame to fabricate various layers. Biocompatible UV crosslinking and chemical genipin crosslinking are two crosslinking methods that can provide mechanical robustness within a desired period of time.

Multi-layered disc-shaped scaffolds can be formed. The thickness of layers and the number of layers affect cell viability and mechanics of multilayered cellularized scaffolds. Chondroitin sulfate (CS, a polysaccharide that is abundant in cartilage) and TGF-β3 (a potent cartilaginous growth factor) are included in the formulation of layers in some embodiments to promote cells to behave like cartilage cells. The concentrations of CS and TGF-β3 are varied systematically to obtain the most effective cell response. Mechanostimulation can be employed in various embodiments to improve diffusion and matrix synthesis by cells. The construct morphology, formulation (CS and TGF-β3 contents) and the mechanical loading regimen that is the most stimulant to cells can be adopted.

The key process variables are electric current density, electrode separation and density of the molecules, nanoparticles and microparticles with ampholytic nature in solution. We have elaborated on the biophysical principles that result in the electrocompaction process via models earlier. These models foresee that the electric current density is critical for the rate of establishment of the pH gradient which in turn determines the charge of molecules. The proximity of electrodes determine the electrostatic field strength acting on the molecules, and closer the electrodes, the greater the electrostatic push on the molecules. Compactant solution density determines the amount of compactant deposited (i.e. the thickness of the layer). But also, at high densities, the viscosity of the solution increases which in turn curbs the molecular mobility. Models can be employed to predict the electric current density, electrode separation and compactant, such as collagen, concentration values to be used in experiments. The degree of compaction (per measurement of thickness before and after compaction) can be measured as a function of increasing electric current density (at 1, 10 and 100 A/cm$^2$, presented results obtained at 1 A/cm$^2$ which provides compaction in minutes over the full field). Following this, at a constant current density level, the electrode separation can be varied from 2 mm down to 0.5 mm. The final stage keeps current and separation constant and vary the compactant concentration. Mechanical properties of resulting sheets can be measured as described later in this section.

Chondroitin sulfate is naturally present in cartilage. It provides additional tone to the matrix by facilitating the absorption of water molecules. Type-II collagen (Elastin Products Company, MO) can be dissolved in 0.01 M acetic acid at a concentration of 3 mg/ml and dialyzed against ultrapure water for 24 hours. Chondroitin Sulfate (CS; Sigma, MO) can be dissolved in ultrapure water at a concentration of 10 mg/ml to make up the stock solution. Composite mixtures of chondroitin sulfate and dialyzed collagen (1:2, 1:4. 1:10 and 1:30; dry weight ratio CS:Collagen) can be prepared prior to loading into the electrochemical cell. Samples can be fabricated as discs (5 mm diameter, 0.5 mm in thickness) by using rubber spacers between carbon electrodes (FIG. 2). For visualization of CS within the scaffold, samples can be serially dehydrated and prepared histologically as we have done before. Briefly, histological sections of the sheets can be incubated in DMMB dye solution (DMMB in water with 40 mM NaCl and 40 mM glycine) for 45 minutes and excess DMMB can be rinsed with ultrapure water. High quality images of the DMMB stained sections can be taken to visualize the distribution of CS within the type-II construct. To quantify the amount of CS incorporated in the construct, the construct can be dissolved in 10 mM HCl and a colorimetric DMMB assay can be performed as we have done before. Briefly, 50 μl of sample can be added to a 96 well plate. To this, 200 μl of DMMB solution can be added and the absorbance can be recorded at 525 nm (Spectramax, Molecular Devices). A standard curve can be generated using known concentrations of CS and the linear equation can be used to determine the amount of CS incorporated within the type-II collagen construct. The swelling ratio of constructs can assessed gravimetrically as a function of CS content.

Baseline material properties can be assessed prior to crosslinking the sheets. For screening purposes compression tests of discs can be conducted using a solids rheology device (Rheometrics) at the stated CS:Collagen ratios (N=10/group). Otherwise, intrinsic property measurements (aggregate modulus, permeability) can be reserved for characterizing formulations which are promising per the outcome of initial screening tests. Discs can be placed on a flat granite surface in wet form and the thickness of gels can be measured at five locations over the surface using a non-contact laser micrometer (Micro-epsilon, Opto NDT). Each sample can be subjected to 2 Hz cyclic loading to obtain storage and loss moduli. This can be followed by a compressive monotonic loading scheme to obtain stress-strain behavior and strength. The deformation can be applied until 20% and sample can be unloaded to zero force to find permanent deformation as a measure of the resilience of the construct at high deformations. Bovine cartilage slices of comparable dimensions act as positive controls and a CS free group acts as the negative control. The concentration of CS with greatest mechanical robustness (storage modulus, strength, loss modulus) can be used in the subsequent crosslinking studies.

Genipin is a non-toxic crosslinking agent that is naturally derived from the jasmine plant. We utilized this crosslinking agent in earlier studies and collagen threads crosslinked as such were biocompatible. Excessive crosslinking prolongs degradation unduly and insufficient crosslinking results in weaker constructs. A goal is to determine the shortest duration of genipin treatment that provides the steady state mechanical stiffness. Specifically, the compacted sheets can be treated in isopropanol for one hour and placed in genipin dissolved in 90% ethanol (0.625%) for 0, 2, 4, 6, 8, 12 and 24 hours. Mechanical properties can be assessed as elucidated.

UV crosslinking has the potential to work out on a shorter time frame (within 30 minutes) and it can be executed more conveniently in mass production form (such as UV exposure of large sheets in chambers). To improve the baseline mechanical properties of CS incorporated type-II collagen cartilage analog sheets, we can mix, for example, two biocompatible UV photoinitiators (riboflavin and VA-086) with the collagen/CS solution prior to electrochemical compaction. The photoinitiators can get trapped in the continuum of the resulting sheet and allow crosslinking of the sheets at lower UV intensities and lower treatment durations. Photoinitiator trapped cartilage-analog sheets can be placed on a reflective surface and exposed to UV radiation. Riboflavin is used clinically to crosslink cornea in patients. The existing literature indicates that the agent absorbs the UV light the most intensely (thus crosslinking the most efficiently) at 366 nm while having minimal damage to resident cells. A radiant energy of 2.5 mW/cm$^2$ is used at 1 cm distance in ophthalmological applications for up to 30 minutes. Based on this knowledge, we can apply riboflavin for example, at three concentrations 0.1%, 0.5% and 2.5% (30 minutes at 2.5 mW/cm$^2$ from 1 cm) with the mid-range value taken from the literature. The treatment time at 5 minutes, 15 minutes and 30 minutes (at 0.5% concentration at 2.5 mW/cm$^2$ from 1 cm can be assessed). Another set of experiments can vary the light intensity at 0.5, 1 and 2.5 mW/cm$^2$ (30 minutes at 0.5% concentration from 1 cm). Cumulatively we can find the trends as a function of concentration, intensity and duration. Based on the outcome of these trends, we can interpolate (or extrapolate) a combination of variables that will give a strong sheet at the lowest possible duration, UV intensity and riboflavin concentration. VA-086 is an azo initiator that is known to be non-toxic for up to 1.5% concentration and it can crosslink collagen. VA-086 can be dissolved in collagen/CS solution at 0.5%, 1% and 1.5% (w/v). The mixture can be subjected to electrochemical treatment to obtain the sheets. Similar to riboflavin model, we can assess the variation in stiffness at different durations, UV intensities and photoinitiator concentrations to identify the optimal combination.

Improvement in mechanical stiffness is expected with incorporation of CS and crosslinking. The current level of stiffness that we have in crosslinked electrocompacted collagen CAS is 0.2 MPa. This value is within 40 percent of the targeted 0.5 MPa, a mid-range value for native cartilage tissue. This proximity provides us with confidence to attain the target stiffness value.

In various embodiments of the invention, cells are seeded on random and ELAC threads at increasing stiffness values. Notably, ELAC threads can be crosslinked to encompass three orders of magnitude of Young's modulus (1 MPa to 1000 MPa), the higher end being comparable to the native tendon. The proliferation, tenocytic differentiation and matrix synthesis by MSCs on threads can be assessed to identify the conditions which maximize the differentiation. Various topographies can be supplemented with dermatan sulfate (DS), a glycosaminoglycan richly present in tendon to enhance the topographical differentiation cues with compositional cues.

An implantable scaffold form is prepared utilizing the biomaterials described herein in a micropatterned electrochemical deposition process. The method unifies computer aided design (CAD) and fabrication to generate patterned electrode pairs which can be used to transform monomeric collagen solutions (and other ECM additives) to solid phase patterned lattice layers, see FIG. 5. Registered assembly of such layers results in scaffolds with interconnected porosity.

In various embodiments, the microarchitecture of lattice patterns is varied to obtain mechanically competent scaffolds with interconnected porosity. These variables include filament area, pore size, filament angles and deposition pattern (linear filaments vs. crimp like sinusoidal filaments). Due to the high number of variables, these combinations can be assessed computationally in the first step via finite element analysis to determine variables which provide a load-displacement curve reflecting the non-linear elastic properties of tendons the closest. The deposition patterns favored by computational analysis can then be fabricated to confirm the outcome by mechanical tests. The suturability of the scaffold can be assessed and suture retention can be improved by local reinforcement of lattice network with biodegradable polymers.

The interconnected porosity allows populating scaffold with cells expeditiously and also facilitates nutrient diffusion. In these experiments, micropatterned scaffolds can be populated with cells and the population rate, proliferation, tenocytic differentiation and matrix synthesis can be assessed over time.

ELAC threads can be synthesized as described herein or known in the art. Briefly, acid soluble monomeric collagen solution (Nutragen) can be diluted two-fold with ultrapure water to 3 mg/mL, dialyzed against ultrapure water for 18 hours, loaded between electrodes and electric current can be applied (30 Volts, 0.1-0.4 A). Aligned collagen can be incubated in 1×PBS for 6 hours to promote fibril formation.

ELAC threads have a Young's modulus of 1 MPa prior to crosslinking. Due to close molecular packing and uniform alignment, covalent crosslinking increases the stiffness 1000-fold, to 1 GPa level. Furthermore, the stiffness can be controlled by changing crosslinking conditions, ELAC threads can be produced with 1 MPa, 10 MPa, 100 MPa and 1,000 MPa modulus values. ELAC threads can be subjected to the following treatments to obtain the desired stiffness: 1) Uncrosslinked ELAC (1 MPa), 2) Uncrosslinked ELAC treated with 90% ethanol for 3 days (10 MPa), 3) ELAC crosslinked in 0.625% genipin in 1×PBS for 3 days (100 MPa) and 4) ELAC crosslinked in 2% genipin in 90% ethanol for 3 days (1000 MPa). Stiffness values of resulting threads can be confirmed by mechanical tests as we have done before. Briefly, ELAC threads in wet state can be loaded monotonically to failure at a strain rate of 10 mm/min. Stress and strain values can be determined from the load and displacement data. Young's modulus (stiffness) can be computed by calculating the slope of the steepest region of the stress-strain curve.

Suitable groups are 1) randomly oriented collagen, 2) randomly oriented crosslinked collagen, 3) oriented collagen thread at 1 MPa, 4) ethanol treated oriented collagen at 10 MPa, 5) oriented collagen crosslinked to 100 MPa, 6) oriented collagen crosslinked to 1000 MPa. These groups will cover a range of stiffness from kPa to GPa, a range of million-fold change in stiffness. Prior studies which assessed stiffness effects analyzed up tens of MPa range, which is far below natural tissues stiffness values (hundreds of MPa to GPa).

Differentiation of MSCs on ELAC threads can be assessed using quantitative real time PCR as we have done before. A sample size of n=10 wells/group/time point can be used. Each well can consist of six 2 cm long ELAC threads. Total RNA can be extracted on days 3, 7, 14 and 28. The expression of tendon specific genes (scleraxis, tenomodulin, thrombospondin) and tendon related genes (collagen type I, collagen type III, COMP, tenascin C, decorin) can be assessed using real-time PCR. To demonstrate the specificity of tenogenic differentiation, the expression of genes specific to lineages other than tendon can also be assessed: Runx2 and osteocalcin (osteogenic), sox9 and collagen type II (chondrogenic), and PPARγ and adiponectin (adipogenic). The fold change in target gene expression can be calculated relative to the expression by cells seeded on polystyrene culture plates.

MSCs and TDFs can be cultured on ELAC threads as described in the previous section. Matrix deposition can be assessed by using quantitative histomorphometry, immunohistochemistry, western blot and transmission electron microscopy (TEM) for example at days 14 and 28. For quantitative histomorphometry and immunohistochemistry, cell-seeded ELAC samples can be fixed, embedded and sectioned in a plane that is perpendicular to the longer axis of ELAC threads. H & E stained sections can be examined to assess cell viability. Masson trichrome stained sections can be used to quantify the area of de novo fibrous tissue deposited by the cells. Sections can also be stained with Safranin O for presence of proteoglycans and with oil-red-o for presence of fat-tissue. Immunohistochemistry can be performed following our previously published protocols to evaluate the type of collagen deposited (collagen type I and collagen type III) and tenascin-C as a tendon related matrix molecule. Presence of biglycan and decorin can be investigated by western blot as described previously. Total protein from the cell seeded ELAC threads can be extracted using a total protein extraction kit (Millipore) and the amount of total protein can be quantified using BCA protein assay kit (Pierce). For TEM, samples can be fixed, embedded, sectioned transversely to the longer axis of ELAC fibers, stained with uranyl acetate and examined with TEM as we have done before. The structural organization and diameter of the newly synthesized collagen fibrils can be measured using Image J (Rasband, W.S., ImageJ, U. S. National Institutes of Health, Bethesda, Md.). Collagen fibrils in ELAC are smaller than 20 nm and distinguishable from cell synthesized collagen fibers which are 100 nm or greater.

Effects of dermatan sulfate incorporation on the differentiation of MSCs can be assessed. Dermatan sulfate (DS) is one of the most ubiquitous GAGs in tendon matrix. It is particularly abundant in tensional regions of tendon. It is implicated in attaching and bridging collagen phase as well as in cell signaling. Therefore, inclusion of DS in ELAC would render a composition that is more convergent to that of tendon's and may synergistically add to the topographical cues in terms of promoting differentiation. In our earlier work, we demonstrated that when collagen-DS mixtures are subjected to electrochemical gradients, DS is mobilized with collagen and becomes trapped in the final ELAC. The experiments include DS in ELAC at various concentrations and assess the effects on mechanical function and cell differentiation. Our earlier experience in inclusion of DS mimics indicated that such molecules do not compromise mechanical properties of ELAC threads and extend the failure strain in uncrosslinked fibers.

DS can be added into the ELAC thread as we have done before. Briefly, composite mixtures of collagen and DS can be prepared for example at three different molar ratios (collagen only (no DS) and 30:1 and 10:1 collagen:DS) prior to loading into the electrochemical cell. The mixture can then be loaded between two electrodes and electric current can be applied (30 Volts, 0.1-0.4 A) to form DS incorporated ELAC thread. The threads can be subjected to PBS treatment and crosslinking. The effect of DS incorporation on the mechanical properties, cell differentiation and matrix production can be assessed.

ELAC bioscaffolds need to meet the mechanical, surgical and morphological demands of future applications. Therefore, the mentioned activities will systematically converge to a 3D scaffold with interconnected porous network with maximal strength, maximal suture retention strength and load-displacement profile that is converging to that of the native tendon. We can also assess the functional baseline in vitro performance of scaffolds sutured in place in an in vitro rabbit shoulder repair model. Other activities can conduct in vitro cell-studies where the timeline for population of scaffolds by cells can be investigated. Furthermore, matrix production and differentiation in this 3D framework can be studied.

Figure 5:
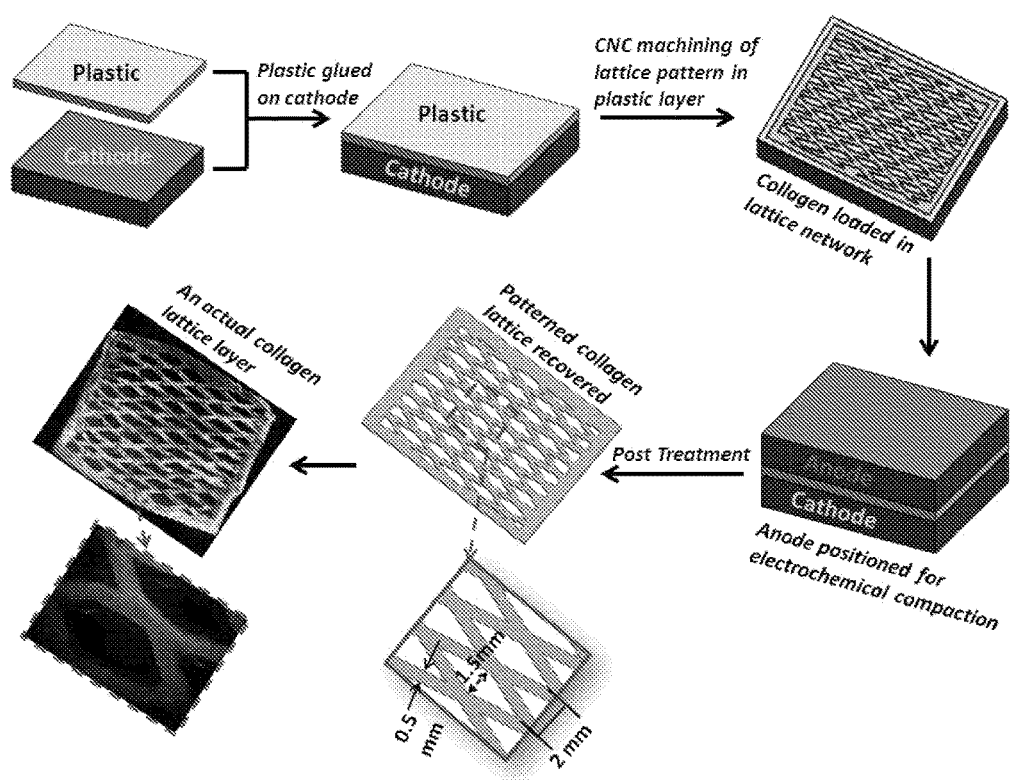
FIG. 5 illustrates patterned electrochemical compaction and alignment of a solution comprising one or more of electrochemically compactable molecules, nanoparticles and microparticles with ampholytic nature, in particular monomeric collagen solutions, as mechanically robust lattice layers.

The number of variables pertaining to the scaffold morphology is large, see FIG. 5; necessitating a preliminary computational screening of mechanical behavior prior to fabricating the materials. The model can simulate load-displacement behavior of the multilayered lattice structure to determine morphologies which provide the nonlinear elastic behavior of tendon (classical toe-in region followed by linear region) as well as those which converge to stiffness of equivalent tendon structures.

The morphological variables of the individual lattice layers are filament cross sectional area and porosity. The lattice morphology will consider linear filaments and sinusoidal filaments (to emulate the crimp pattern inherent in tendon). For any given lattice morphology, the simulations can be executed, for example, at three levels of filament area (500 µm, 750 µm, and 1000 µm), two levels of porosity (500 µm and 1000 µm) and two levels of filament angles (15° and 30° to the vertical). When lattice layers are overlaid in staggered fashion, the effective pore size becomes 250 and 500 µm, respectively. The lower size porosity is big enough to accommodate arterioles and bulk of cells. It is commensurate with ideal pore size for bone replacement materials. The simulation scenarios cover the range of cases bracketed by 'high number of small filaments with low porosity' to low number of larger filaments with high porosity'. The former situation provides a greater surface area, better damage tolerance with possibly greater strength but at the expense of slowing cell and nutrient transport. The latter case would behave vice versa. The simulations aim to obtain the greatest level of porosity that provides mechanically suitable outcome. Each lattice layer, as fabricated, is 500 microns in thickness. Ten layers can be fused in the simulations in a staggered fashion (FIG. 6), to obtain the final 3D scaffold in a thickness of 5 mm, commensurate with the thickness of RIT.

Transverse isotropy can be assumed in FEM analysis. Individual threads can be loaded under a stage fitting on microscope stage (Fullam Inc.) and the longitudinal and transverse deformations can be recorded and processed to obtain Young's modulus and Poisson's ratios in planes along and perpendicular to the longer axis of threads. The stiffness matrix components can be calculated using these experimental values and entered into the FEM software (ABAQUS). The end region of lattice can be emulated as potted in a polymer matching the properties of the fiber itself and loading can be performed up to 50 N in incremental steps. The resulting deformation at each increment can be noted to obtain the load displacement curve for each scenario. The load-displacement profile that is the most convergent to the load displacement profile of RIT can be selected. We can also assess stress distribution to identify critically loaded regions in these configurations.

Figure 6:
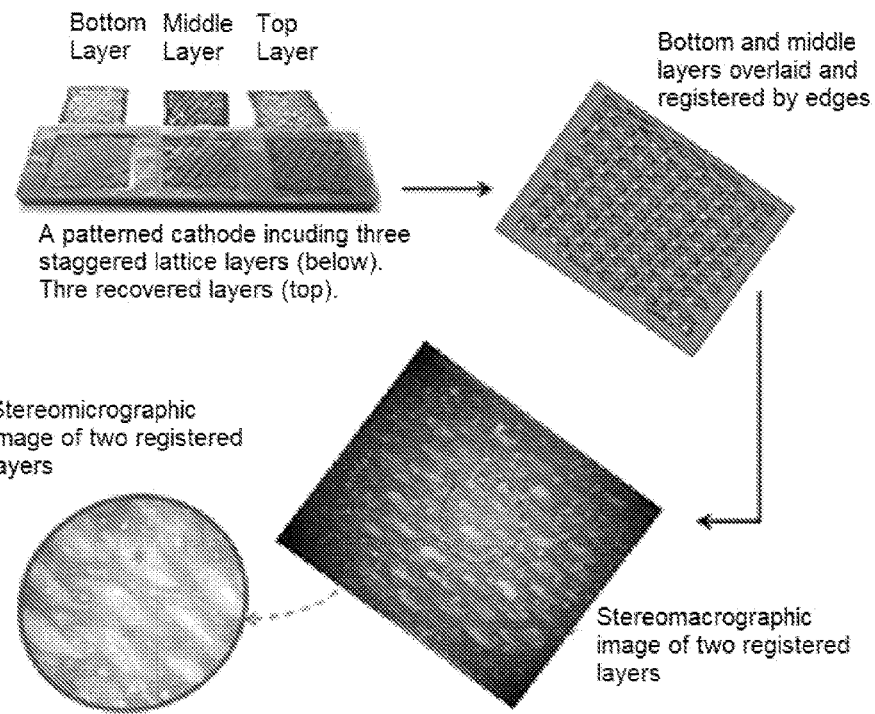
FIG. 6 illustrates 3D-scaffolds that can be obtained by overlaying and crosslinking the individual lattice layers.

Fabrication can be performed using the lattice morphology based on the outcome of FEM simulations. Overall dimensions of the scaffold can be 10×10×5 mm in accordance with the dimensions of RIT. We have already produced machined patterned electrode structures, see FIG. 6 and generated individual lattice layers, see FIG. 5. Layers are placed on top of each other in register to obtain the final scaffolds as shown in FIG. 6. The adhesion between layers occurs during genipin crosslinking stage.

What can be added to the compactant, for example collagen, as additional phases is not limited to dermatan sulfate. In more general terms, one can put any glyscoaminoglycan and proteoglycans to these processes without changing the processing outcome. Also, one can incorporate bone-like mineral particles (such as hydroxyapatite) to the compactant, e.g. collagen, and perform all of these processes to have bone replacement materials, see FIG. 4. We can also integrate bone-like and tendon-like threads to make bone-tendon replacements.

The present invention also relates to electrocompacted sheets having a tuned stiffness anisotropy and methods for producing the same. As utilized herein stiffness anisotropy refers to providing a material with different stiffness values in different material directions. Stiffness anisotropy is present in many tissues including muscle, bone and tendons. A method of the present invention includes inducing surface anisotropy by stretching an electrocompacted sheet or form. The electrocompacted material can be stretched in an amount up to 75% percent of its original dimension, such as length or width. Specific examples are set forth herein.

Type-I collagen solution was electrocompacted as sheets between planar electrodes. Surface anisotropy (SA) was induced by stretching the sheets longer by 25%, 50% and 75%. Collagen alignment with stretch was assessed by compensated polarized imaging (blue color indicates alignment in SW-NE direction). Samples were tested in uncrosslinked form or after crosslinking in genipin. Samples were tested in tension along ($L$) and transverse ($T$) to the stretch direction. Moduli in the longitudinal ($E_L$) and transverse ($E_T$) directions were calculated as the slope of the linear region. Stiffness anisotropy was expressed as SA=($E_L/E_T$).

Molecular alignment increased gradually with stretch as indicated by the emergence of blue color in the polarized images (FIG. 12A). SEM images also indicated the collagen fibril alignment along stretching direction (FIG. 12B). SA was tunable by up to 10-fold and the stiffness values were tunable by 100-fold by using stretching and crosslinking processes (FIGS. 12C& D). This amounts to creation of a material profile where the modulus can be changed from several hundred kPa, to single digit MPa, to hundred MPa. Cell morphologies on substrate with higher SA values were more elongated (FIG. 12E).

The following represent additional examples of fabrication of 3D-complex solid forms by electrochemical compaction of compactant rich solutions.

Electrochemical Fabrication:

A 12.5 mm diameter hemispherical indent was milled in a carbon electrode which was connected as the cathode. The indent was filled with type-I collagen solution (Advanced Biomatrix, CA). An aluminum ball of 10 mm diameter, positioned concentrically within the hemispherical indent, served as the anode. Electrical current compacts the molecules close to the cathode. On the top of the electrocompacted pure collagen layer, a mixture of hydroxyapatite (HA) and type-I collagen solution (60% w/w HA) was compacted as a second layer. The more complex structure of the nose, see FIG. 7, was fabricated by molding liquid metal as electrodes.

Effects of ECOMP on Mechanical Properties:

Type-I collagen solution was loaded between two parallel planar carbon sheet electrodes to obtain disc shaped sheets. Sheets were crosslinked in 0.635% genipin in 90% ethanol for 3 days, tested under compression (1%/sec) to obtain the modulus (RSAII, Rheometrics Inc., Piscataway, N.J.).

Cell Response to Electrocompacted Collagen:

Human MSCs were sandwiched between two compacted type-I collagen sheets and cell viability was determined at day 2 using live-dead assay. Further, electrocompacted type-II collagen (Elastin Products Company, MO) sheets were seeded with human MSCs at high density ($1\times10^6$ cells/cm$^2$) and cultured under chondrogenic culture conditions (with TGF-β3) for 21 days. Chondrogenic differentiation was assessed by Safranin O staining at the end of the culture period.

Figure 7:
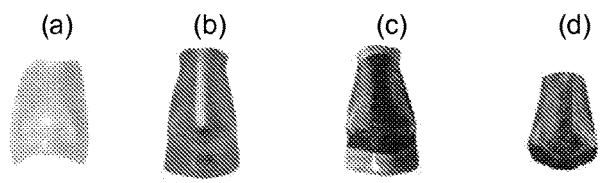
FIG. 7 illustrates a further embodiment of various components used in fabrication of a 3D-complex solid form by electrochemical compaction including a) anode, b) cathode, c) collagen compacted onto cathode and d) electrochemically fabricated scaffold standing alone, wherein the scaffold produced is in the form of a nasal shell structure.
Figure 8:
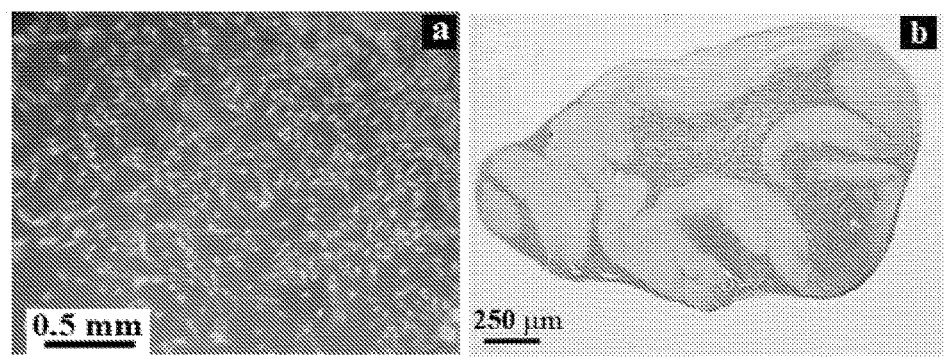
FIG. 8 illustrates a further embodiment including a) cell viability on electrochemically compacted type-I collagen sheets, b) cellular regions were positive for safranin O (red) on electrocompacted type-II collagen sheets.

Electrochemical compaction of collagen and hydroxyapatite-collagen solution using curved electrodes resulted in a mechanically robust, bilayered scaffold with curved topography, see FIGS. 4 and 7. Similar to the hemispherical shell, the nasal shell structure maintained its form.

The modulus of compacted sheets (100 kPa) was 20-fold higher compared to uncompacted collagen gels (<5 kPa). Cell viability of human MSCs was maintained when sandwiched between two sheets FIG. 9(a) suggesting that the compacted collagen sheets are biocompatible. Safranin O staining revealed rich presence of glycosaminoglycans indicated that electrocompacted type-II collagen sheets support chondrogenic differentiation of human MSCs.

The electrochemical-compaction process can deposit 3D-freeform collagen layers simultaneously and rapidly (within 1 minute). Resulting layers can be seeded with cells and stacked sequentially to obtain cellularized complex tissue/organ forms. This method also emulates the compositional complexity of tissues by allowing the inclusion of additives such as mineral particles, other biomolecules and bioinductive growth factors. Therefore, electrochemical compaction can be used for the repair of joints, craniofacial defects and dental complications.

In accordance with the patent statutes, the best mode and preferred embodiment have been set forth; the scope of the invention is not limited thereto, but rather by the scope of the attached claims.

What is claimed is:

1. A device for producing an electrochemically aligned strand, comprising:
a pump system including a) a pump, b) a solution reservoir for a solution comprising one or more of electrochemically alignable molecules, nanoparticles and microparticles with ampholytic nature, and c) an outlet;
a rotatable drum having a circumferential groove adapted to receive a portion of the solution from the outlet of the solution reservoir, wherein at least two substantially parallel electrodes are present in the groove on opposite side of the grove, the electrodes encircling the circumferential groove, wherein the outlet is positioned at a top of the drum such that the solution is applyable to the circumferetial groove of the drum at a position that ranges from vertical to an angle of about 60° from vertical measured from a line extending from a center of the drum to a vertical top of the drum, and wherein the electrochemically aligned strand is formed in the groove from the solution received in the circumferential groove upon transmission of an electric current to the at least two electrodes; and
a collection device positioned relative to the drum such that the electrochemically aligned strand formed on the drum is collected by the collection device.

2. The device according to claim 1, wherein the at least two electrodes comprise parallel electrode wires, and wherein the rotation of the drum is actuated by a motor that is present and operatively connected to the drum.

3. The device according to claim 2, wherein the electric current is supplied to the at least two electrodes on the rotating drum in a wire-free fashion utilizing sliding metal contacts in contact with the at least two electrodes.

4. The device according to claim 2, wherein the collection device includes a collection spool that is situated in a liquid bath present in a collection reservoir.

5. The device according to claim 4, wherein the device includes a microprocessor, wherein one or more of a flow rate from the solution reservoir, a rotational speed of the collection spool and a rotational speed of the rotatable drum are differentially controlled by the microprocessor.

6. The device according to claim 2, wherein the pump controls the flow rate of the solution from the solution reservoir.

7. The device according to claim 6, wherein the outlet is positioned to transfer the solution to the drum at a position that ranges from the vertical top of the drum to an angle of about 45°.

8. The device according to claim 7, wherein the device includes a plurality of electrode sets, with each set located in a separate groove thereby allowing multiple electrochemically aligned strands to be fabricated simultaneously.

9. A method for producing an electrochemically aligned strand, comprising the steps of:
obtaining a device according to claim 1;
filling the solution reservoir with a quantity of solution comprising one or more electrochemically alignable molecules, nanoparticles and microparticles with ampholytic nature;
applying the solution to a portion of the drum;
applying an electric current to the solution during rotation of the drum to induce electrochemical alignment;
and transferring an electrochemically aligned strand formed on the drum from the solution to the collection device.

10. The method according to claim 9, wherein the collection device includes a bath comprising phosphate buffered saline that induces D-banding to the strand transferred to the collection device, further including the step of winding the strand on a collection spool situated in the bath of the collection device, wherein the solution is transferred into the circumferential groove on the drum, and wherein the solution rotates on the drum while being transformed into the electrochemically aligned strand, and further including the step of differentially controlling one of more of a flow rate from the syringe, a rotational speed of the collection spool and a rotational speed of the drum utilizing a microprocessor.

11. The method according to claim 9, further including the step of crosslinking the formed electrochemically aligned strand.

12. The method according to claim 9, further comprising the steps of:
weaving or braiding an electrochemically aligned structure with the strand.

13. The method according to claim 12, further including the step of impregnating a quantity of polylactic acid into an end of the woven or braided structure, wherein impregnation is achieved by dipping an end region of the structure in a solution including dissolved polylactic acid.

* * * * *